United States Patent
Geerts-Ossevoort et al.

(10) Patent No.: US 9,618,594 B2
(45) Date of Patent: Apr. 11, 2017

(54) CONTRAST ENHANCED MAGNETIC RESONANCE ANGIOGRAPHY WITH CHEMICAL SHIFT ENCODING FOR FAT SUPPRESSION

(75) Inventors: Liesbeth Geerts-Ossevoort, Veldhoven (NL); Hendrik Kooijman, Hamburg (DE); Eveline Alberts, Leystad (NL); Holger Eggers, Ellerhoop (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 769 days.

(21) Appl. No.: 14/112,585

(22) PCT Filed: Apr. 17, 2012

(86) PCT No.: PCT/IB2012/051902
§ 371 (c)(1),
(2), (4) Date: Oct. 18, 2013

(87) PCT Pub. No.: WO2012/143847
PCT Pub. Date: Oct. 26, 2012

(65) Prior Publication Data
US 2014/0043022 A1 Feb. 13, 2014

(30) Foreign Application Priority Data
Apr. 21, 2011 (EP) .................................. 11163418

(51) Int. Cl.
*G01R 33/48* (2006.01)
*A61B 5/02* (2006.01)
(Continued)

(52) U.S. Cl.
CPC ...... *G01R 33/4828* (2013.01); *A61B 5/02007* (2013.01); *A61B 5/055* (2013.01);
(Continued)

(58) Field of Classification Search
CPC ............ G01R 33/4828; G01R 33/5635; G01R 33/5601; G01R 33/56308; G01R 33/5615;
(Continued)

(56) References Cited

U.S. PATENT DOCUMENTS

| 5,873,825 A | 2/1999 | Mistretta |
| 6,845,260 B2 | 1/2005 | Liu |

(Continued)

FOREIGN PATENT DOCUMENTS

| WO | 0072037 A1 | 11/2000 |
| WO | 2010113048 A1 | 10/2010 |

OTHER PUBLICATIONS

Shat et al "3T Coronary MRA Using 3D Multi-Interleaved Multi-Echo Acquisition and Varpro Fat-Water Separation" Proc. Intl. Soc. Mag. Reson. Med. 18 (2010) p. 3667.
(Continued)

*Primary Examiner* — G. M. Hyder

(57) ABSTRACT

The invention relates to a method of performing contrast enhanced first pass magnetic resonance angiography, the method comprising: acquiring (302) magnetic resonance datasets of a region of interest using a single- or multi-echo data acquisition technique, wherein the echo times of the one or multiple echoes are flexible, wherein at the time of the data acquisition the region of interest comprises fat, water and a contrast agent, processing (304) the datasets using a generalized Dixon water-fat separation technique to eliminate the signal originating from the fat from the background for reconstruction of an image data set.

11 Claims, 3 Drawing Sheets

(51) Int. Cl.
  *G01R 33/56* (2006.01)
  *G01R 33/563* (2006.01)
  *A61B 5/055* (2006.01)
  *G01R 33/561* (2006.01)
  *G01R 33/565* (2006.01)

(52) U.S. Cl.
  CPC ..... *G01R 33/5601* (2013.01); *G01R 33/5635* (2013.01); *G01R 33/56308* (2013.01); *G01R 33/5615* (2013.01); *G01R 33/56563* (2013.01)

(58) Field of Classification Search
  CPC .......... G01R 33/56563; A61B 5/02007; A61B 5/055
  See application file for complete search history.

(56) References Cited

U.S. PATENT DOCUMENTS

| | | | |
|---|---|---|---|
| 7,343,193 | B2 | 3/2008 | Block et al. |
| 7,660,618 | B2 | 2/2010 | Abe |
| 7,706,855 | B1 | 4/2010 | Priatna |
| 8,774,475 | B2 | 7/2014 | Brendel et al. |
| 2008/0125652 | A1 | 5/2008 | Clark |
| 2010/0195885 | A1* | 8/2010 | Ma ............... G01R 33/4828 382/131 |
| 2012/0301000 | A1* | 11/2012 | Bornert ............ G01N 24/082 382/130 |

OTHER PUBLICATIONS

Eggers "Influence and Compensation of Fat Signal Dephasing and Decay in Two-Point Dixon Imaging" Proc. Intl. Soc. Mag. Reson. Med 18 (2010) p. 2924.

Michaely et al, "Feasibility of Gadofosveset-Enhanced Steady-State Magnetic Resonance Angiography of the Peripheral Vessels at 3 Tesla With Dixon Fat Saturation" Investigative Radiology 2008 43(9) p. 635-641.

Ma, Jingfei "A Single-Point Dixon Technique for Fat-Suppressed Fast 3D Gradient-Echo Imaging with a Flexible Echo Time", Journal of Magnetic Resonance Imaging, vol. 27, 2008, pp. 881-890.

Xiang, Qing-San "Two-Point Water-Fat Imaging with Partially-Opposed-Phase (POP)) Acquisition: An Asymmetric Dixon Method", Magnetic Resonance in Medicine, vol. 56, 2006, pp. 572-584.

Michaely, Henrik J. et al "Feasibility of Gadofosveset-Enhanced Steady-State Magnetic Resonance Angiography of the Peripheral Vessels at 3 Tesla with Dixon Fat Saturation", Investigative Radiology, vol. 43, No. 9, Sep. 2008, pp. 635-641.

Yasua Amano, MD et al "Fat-Suppressed Three-Dimensional MR Angiography Technique with Elliptical Centric View Order and No Prolonged Breath-Holding Time", Journal of Magnetic Resonance Imaging, vol. 16, 2002, pp. 707-715.

Eggers, Holger et al "Dual-Echo Dixon Imaging with Flexible Choice of Echo Times", Magnetic Resonance in Medicine, vol. 65, 2011, pp. 96-107.

* cited by examiner a) b)

CONTRAST ENHANCED MAGNETIC RESONANCE ANGIOGRAPHY WITH CHEMICAL SHIFT ENCODING FOR FAT SUPPRESSION

CROSS-REFERENCE TO PRIOR APPLICATIONS

This application is the U.S. National Phase application under 35 U.S.C. §371 of International Application No. PCT/IB2012/051902, filed on Apr. 17, 2012, which claims the benefit of European Patent Application No. 11163418.4, filed on Apr. 21, 2011. These applications are hereby incorporated by reference herein.

TECHNICAL FIELD

The invention relates to a method of performing contrast enhanced first pass magnetic resonance angiography, a computer program product, as well as a magnetic resonance imaging apparatus for performing contrast enhanced first pass magnetic resonance angiography.

Image-forming MR methods which utilize the interaction between magnetic field and nuclear spins in order to form two-dimensional or three-dimensional images are widely used nowadays, notably in the field of medical diagnostics, because for the imaging of soft tissue they are superior to other imaging methods in many respects and do not require ionizing radiation and they are usually not invasive.

BACKGROUND OF THE INVENTION

According to the MR method in general, the body of a patient or in general an object to be examined is arranged in a strong, uniform magnetic field $B_0$ whose direction at the same time defines an axis, normally the z-axis, of the coordinate system on which the measurement is based. The magnetic field produces different energy levels for the individual nuclear spins in dependence on the applied magnetic field strength which spins can be excited (spin resonance) by application of an alternating electromagnetic field (RF field) of defined frequency, the so called Larmor frequency or MR frequency. From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicularly to the z-axis, so that the magnetization performs a precessional motion about the z-axis.

Any variation of the magnetization can be detected by means of receiving RF antennas, which are arranged and oriented within an examination volume of the MR device in such a manner that the variation of the magnetization is measured in the direction perpendicular to the z-axis.

In order to realize spatial resolution in the body, linear magnetic field gradients extending along the three main axes are superposed on the uniform magnetic field, leading to a linear spatial dependency of the spin resonance frequency. The signal picked up in the receiving antennas then contains components of different frequencies which can be associated with different locations in the body. The signal data obtained via the receiving antennas corresponds to the spatial frequency domain and is called k-space data. The k-space data usually includes multiple lines acquired with different phase encoding. Each line is digitized by collection a number of samples. A set of samples of k-space data is converted to an MR image, e.g. by means of Fourier transformation.

Magnetic resonance angiography (MRA) has been shown to allow accessing the status of arteries and blood vessels of patients. In the present invention, contrast-enhanced MRA (CE-MRA) is considered, in which MR images are acquired during the arterial first pass of a paramagnetic contrast agent after intravenous injection. However, the intravenous injection itself is not part of the invention.

In conventional contrast-enhanced MR angiography background suppression is obtained by repetitive RF pulses. In this way, most background signal is effectively suppressed except for the fat signal. In order to also suppress the fat signal, which might obscure the vasculature of interest, generally two acquisitions are made: one before injection of the contrast agent—the so called 'mask' image—, and one during presence of the contrast agent. The mask image is then subtracted from the contrast image to eliminate the fat signal.

Although conventional CE-MRA using subtractions as described above has been used for many years, there are several disadvantages to the technique. First at all, this technique requires 2 acquisitions, namely one before and one after contrast agent injection, which increases total scan time. Further, in case motion occurs between the mask and the contrast scans, a subtraction of the resulting images might not be possible due to misalignment of some image features. This problem may even become more severe in areas where a breath hold is required in this case subtraction is difficult, as two breath holds are never identical.

An alternative to subtracting the fat signal from the images is to perform fat suppression during the acquisition of the MRA images. For fat suppression various types of approaches are known. For example chemical shift selective pre-saturation (SPIR, SPAIR) or chemical shift selective excitation strategies can be applied to either suppress or not excite fat signal However, these pulses are too time consuming to build into a CE-MRA scan, as the available scan time is very limited in first pass imaging.

An alternative approach to eliminate the fat signal from the images would be to use water-fat separation by the Dixon method. However, the conventional Dixon method is not well suited for contrast-enhanced MR angiography, since it requires the acquisition of two echoes at echo times, at which water and fat signals are in- and opposed-phase. This leads to long echo times (TEs) and thus to long repetition times (TRs), rendering the timing of the acquisition with arrival of the contrast agent in the region of interest impossible. The conventional Dixon method can therefore generally not be used for CE-MRA, as the technique is too slow.

From the forgoing it is readily appreciated that there is a need for an improved MR imaging method. It is consequently an object of the invention to enable MR imaging in a fast manner by providing CE-MRA images with fat suppression for first pass imaging. Further, from the forgoing it is readily appreciated that there is a need for an improved MR imaging system and an improved computer program product adapted to carry out the method according to the invention.

SUMMARY OF THE INVENTION

In accordance with the present invention a method of performing contrast-enhanced first pass magnetic resonance angiography is provided, wherein the method comprises acquiring magnetic resonance datasets of a region of interest using a single- or multi-echo data acquisition technique, wherein the echo times of the one or multiple echoes are flexible, wherein at the time of the data acquisition the region of interest comprises fat, water and a contrast agent. Further, the method comprises processing the datasets using a generalized Dixon water-fat separation technique to eliminate the signal originating from the fat from the background for reconstruction of an image data set.

Embodiments of the invention have the advantage that CE-MRA can be performed with fat suppression in a fast and reliable manner. The invention enables to produce an angiographic image data set of blood vessels only, without the need for a separate baseline scan. Moreover, fat signal is highly effectively eliminated.

For the present invention it is essential that the echo times can be chosen freely as compared with conventional Dixon methods. Since the echo times of the one or multiple echoes are flexible, i.e. not fixed to times at which water and fat signals are in- or opposed-phase, these echo times can be chosen to be much shorter such that a significantly shorter TR results. As a consequence, accurate timing of the acquisition with arrival of the contrast agent in the region of interest is easily possible. The data acquisition can thus be started and completed while the contrast agent is present in the region of interest, namely in the arteries of the object to be examined. Since the method is performed for 'first pass' imaging—i.e. arterial only imaging during the initial injection of the contrast agent, timing of the acquisition is of crucial importance since the time available for selective depiction of the arteries is only about 15 seconds.

Thus, the applied first pass imaging is in sharp contrast to so called 'steady-state' imaging, where timing of the acquisition is not crucial anymore. For example, Invest Radiol. 2008 September; 43(9):635-41, "Feasibility of gadofosveset-enhanced steady-state magnetic resonance angiography of the peripheral vessels at 3 Tesla with Dixon fat saturation", Michaely H J, Attenberger U I, Dietrich O, Schmitt P, Nael K, Kramer H, Reiser M F, Schoenberg S O, Walz M. discloses a combination of contrast enhanced MRA with Dixon image reconstruction. However, this was performed during the steady state 50 minutes after a gadofosveset injection and did not aim to depict the arterial vasculature selectively. Instead, both arteries and veins are depicted. Therefore, in this case timing of the acquisition is not important any more.

In contrast, as mentioned above, since the above described method is performed for 'first pass' imaging timing of the acquisition is of crucial importance and the critical maximum time limit for completion of the data acquisition is 2 orders of magnitude lower than in case of steady-state imaging.

The only limitation on the above described technique is given by the maximum available power of the gradient system used for performing MRA. The technical features of the gradient system directly limit the minimal echo times used in the single- or multi-echo data acquisition technique and thus the achievable image resolution. Thus, embodiments according to the invention permit to acquire signal components from fat and water, i.e. blood with contrast agent, at different relative phases within one TR.

In accordance with an embodiment of the invention, the method further comprises applying a steady-state magnetization pulse sequence for short $T_1$ chemical species, for example tissue, to the region of interest such that additionally signal components from tissue are suppressed.

In accordance with an embodiment of the invention, in case of a multi-echo data acquisition the multi-echo data acquisition technique is a dual-gradient-echo data acquisition technique and the generalized Dixon water-fat separation technique is a two-point Dixon technique with flexible echo times. Further, in case of a single-echo data acquisition the single-echo data acquisition technique is a single-gradient-echo data acquisition technique and the generalized Dixon water-fat separation is a one-point Dixon technique.

An example of a two-point Dixon technique with flexible echo times is given in WO 2010/113048 A1 and Magn Reson Med. 2011 January; 65(1):96-107 "Dual-echo Dixon imaging with flexible choice of echo times", Eggers H, Brendel B, Duijndam A, Herigault G which documents are hereby incorporated by reference. These techniques are also known as "mDixon reconstruction technique".

In accordance with an embodiment of the invention, the acquisition of the magnetic resonance datasets comprises acquiring first and second echo data at the two different echo times resulting in a first and second signal dataset, wherein the first and second echo data is acquired in one time of repetition. By choosing the used echo time(s) short, TR can be kept to a short value. As a consequence, due to the omission of data acquisition before and after contrast agent bolus administration and baseline subtraction, even highly time critical CE-MRA can be performed. This includes data acquisition from regions of interest with potential movement due to for example breath hold techniques, as well as acquisition from regions of interest with continuous movement by cardiac motion.

In accordance with a further embodiment of the invention, the processing of the datasets comprises calculating first and second components, or ratios or fractions of them, from the first and second signal datasets, deriving two differential phase error candidates from the first and second components, selecting, for each pixel, one of the derived differential phase error candidates, based on an assumption of smoothness of disturbing field inhomogeneity and reconstructing a water image using the selected differential phase error candidate.

The following description is provided to further explain the function of the separation algorithm(s) using the modified Dixon technique, with regard to the specific example of fat (e.g., lipid) and water (e.g., in non-fatty tissue) in a subject subjected to an MR scan. This description is in compliance with in WO 2010/113048 A1 and Magn Reson Med. 2011 January; 65(1):96-107. Using the modified Dixon technique, two signals I1 and I2, measured at two different echo times, are mathematically described as follows:

$$I_1 = (W + Fe^{i\Theta_1})e^{i\phi_1} \quad (1)$$

$$I_1 = (W + Fe^{i\Theta_2})e^{i\phi_2} \quad (2)$$

where W and F are the contribution of water and fat, respectively, to the overall signal (W and F are thus positive real numbers), •1 and •2 are the known water-fat angles at the two echo times, and •1 and •2 represent phase errors (e.g., for the respective signals) due to system imperfections, such as main field inhomogeneities and the like. Since the values of the phase errors are unknown, a direct determination of W and F from Equations (1) and (2) is not possible. Thus, at this point, the processor estimates a "big" component B and a "small" component S of the respective signals, from equations (1) and (2). The signal components B and S may be stored to the memory 16 as intermediate data 40. One of the components B and S represents W and the other F, but the mapping is unknown until further processing. Therefore, the phase errors are determined to resolve this mapping problem.

In conventional approaches to two-point Dixon water-fat separation, the estimation of the phase errors is based on the assumption that they are spatially smooth functions, i.e. they change only slowly over the field of view. The extent to which this assumption is true depends on the magnitude of the phase errors. Since •2 can be split up into the phase error •1 and a smaller differential phase error ••, which fulfills the smoothness assumption much better than •2, the estimation is simplified by choosing •1=0, which causes Equations (1) and (2) to be modified as follows:

$$I_1 = (W+F)e^{i\phi_1} \quad (3)$$

$$I_2 = (W+Fe^{i\Theta_2})e^{i(\phi_1+\Delta\phi)} \quad (4)$$

In this case, the phase of I1 equals the phase error •1, which can be corrected as follows:

$$J_1 = (W+F) \quad (5)$$

$$J_2 = (W+Fe^{i\Theta_2})e^{i\Delta\phi} \quad (6)$$

At this point, the differential phase error •• (e.g., the difference between •1 and •2) remains to be found. Using Equation (6), two candidates for •• are computed: one candidate is calculated assuming that the "big" component B is water and the "small" component S is fat, and the other candidate is calculated assuming S is water and B is fat, such that:

$$e^{i\Delta\varphi_1} = \frac{J_2}{B+Se^{i\Theta_2}} \quad (7)$$

$$e^{i\Delta\varphi_2} = \frac{J_2}{S+Be^{i\Theta_2}} \quad (8)$$

The true mapping of B and S to W and F is spatially varying, i.e. it can be different from pixel to pixel. Thus, •• is chosen from the two candidates for each pixel separately, such that the overall solution is as smooth as possible. This approach, which presupposes that •2 mod • •0, is known (see, e.g., Xiang Q S. Two-point water-fat imaging with partially-opposed-phase (POP) acquisition: an asymmetric Dixon method. Magn Reson Med 2006; 56:572-584.). Once •• is estimated, it can be eliminated from Equation (6), and W and F can be calculated from Equations (5) and (6).

In accordance with a further embodiment of the invention, the first and second echo signal datasets are a first and second acquired complex dataset, wherein the processing of the acquired magnetic resonance datasets comprises modelling the first and second acquired complex signal dataset by employing a spectral signal model of fat, said modelling resulting in a first and second modelled complex dataset, said first and second modelled dataset comprising a first and second phase error and the separate signal datasets for water and fat, and determining from the first and second acquired complex dataset and the first and second modelled complex dataset the separate signal dataset for water.

In other words, in this embodiment more complex models of the spectrum of water and fat are incorporated into the separation of two-point methods. It thus permits enhancing the accuracy of a signal separation for water and fat.

In accordance with an embodiment of the invention, the determination of the separate signal datasets for water and fat is performed by minimizing the residuum between the first and second acquired and modelled datasets, where the latter are based on the spectral signal model of at least one of the chemical species. In the exemplary case of two chemical species, two complex equations, i.e. four total equations, are available, wherein the four unknowns in these four equations are the two separate signal datasets for water and fat and the first and second phase error. Consequently, by employing standard mathematical equation solving techniques including numerical techniques, from these four nonlinear equations the two separate signal datasets for water and fat can be obtained.

In accordance with a further embodiment of the invention, the determination of the separate signal datasets for water and fat comprises:

determining the magnitude of the first and second acquired dataset and retrieving an initial estimate of the separate signal datasets for water and fat based on the first and second modelled dataset, deriving from the first and second acquired dataset and the initial estimate of the separate signal datasets for water and fat at least one solution for the difference between the first and the second phase error based on the first and second modelled dataset, determining from the first and second acquired dataset and one solution for the difference between the first and the second phase error the final estimate of the separate signal datasets for water and fat.

This further simplifies the mathematical process of deriving the first and second phase error and the separate signal datasets for water and fat.

In accordance with an embodiment of the invention, the determination of the final estimate of the separate signal datasets for water and fat involves solving a system of two complex equations for two complex separate signals for water and fat.

In accordance with a further embodiment of the invention, the initial estimation of the separate signal datasets for water and fat comprises solving a system of two quadratic equations formed by the magnitude of the first and second acquired and modelled complex datasets. For example, this may be performed employing a biquadratic equation which permits to perform the retrieval of the separate signal datasets in a mathematically simple and thus fast manner. This further permits to speed up the signal separation process for water and fat.

In accordance with a further embodiment of the invention, the determination of the difference between the first and the second phase error results in a true and a false solution, wherein the method further comprises determining the true solution for example based on the assumption of smooth spatial variation of the main field inhomogeneities. In general, for the selection of the correct phasor value, any of a number of known methods, such as the regional iterative phasor extraction (RIPE), may be applied (compare for example Xiang Q S. Two-point water-fat imaging with partially-opposed-phase (POP) acquisition: an asymmetric Dixon method. Magn Reson Med 2006; 56:572-584).

It has to be noted, that throughout the description a phase error is understood either as an error of a phase itself, as well as an error of the respective phasor associated with a given phase.

In accordance with a further embodiment of the invention, the modelling of the first and second dataset comprises employing a linear combination of the separate signal datasets for water and fat, multiplied by a first and second phasor, the first and second phasor comprising the first and second phase error, wherein the weights for the linear combination are derived from the spectral signal model of the chemical species.

This type of modelling has the advantage that the separate signal datasets for water and fat can be obtained from just two different images, none of which needs to be in phase. Consequently, less restrictive assumptions regarding a Dixon reconstruction process need to be applied which enhances the quality of the reconstructed separate signal datasets for water and fat.

In accordance with a further embodiment of the invention, the determination of the separate signal datasets for water and fat is performed using the first and second magnitude, as well as the conjugate complex product of the two acquired datasets. Alternatively, a linear system of two equations may be solved by solely employing the first and second acquired dataset and the difference in the first and second phase error, i.e. without using the first and second magnitude. Since solving a linear system of two equations can be performed in a rather fast manner, a respective reconstruction process is further sped up. In addition, this approach adds one degree of freedom to the solution, which may help to reduce artifacts.

In accordance with a further embodiment of the invention, the spectral signal model is a multi-peak spectral model of fat. Consequently the present invention does not simply assume that only one dominant spectral peak of fat is present in the spectrum but rather employs a multi-peak spectral model of fat. In case only one of the chemical species, for example fat, is modelled, water may be considered as a single-peak spectrum.

Consequently it is assumed that for one of the species, for example fat, the relative resonance frequencies and the relative resonance strengths are known in advance, e.g. obtained from a theoretical or experimental model, or from a separate or integrated calibration, e.g. based on an identification of pixels that likely contain one chemical species like fat only.

In accordance with a further embodiment of the invention, the first and second phase error of the first and second acquired dataset comprises a phase error of the first and second image dataset excluding a chemical shift induced phase error due to the presence of said chemical species modelled by the spectral signal dataset model, i.e. for example excluding a chemical shift induced phase error due to the presence of fat.

In another aspect, the invention relates to a magnetic resonance imaging apparatus for performing contrast enhanced first pass magnetic resonance angiography, the scanner being operable for acquiring magnetic resonance datasets of a region of interest using a single- or multi-echo data acquisition technique, wherein the echo times of the one or multiple echoes are flexible, wherein at the time of the data acquisition the region of interest comprises fat, water and a contrast agent, and processing the datasets using a generalized Dixon water-fat separation technique to eliminate the signal originating from the fat from the background for reconstruction of an image data set.

The method of the invention can be advantageously carried out in most MR devices in clinical use at present. To this end, it is merely necessary to utilize a computer program by which the MR device is controlled such that it performs the above explained method steps of the invention. The computer program may be either present on a data carrier or be present in a data network so as to be downloaded for installation in the control unit of the MR device. Therefore, the invention also relates to a computer program product comprising computer executable instructions to perform the method as described above.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
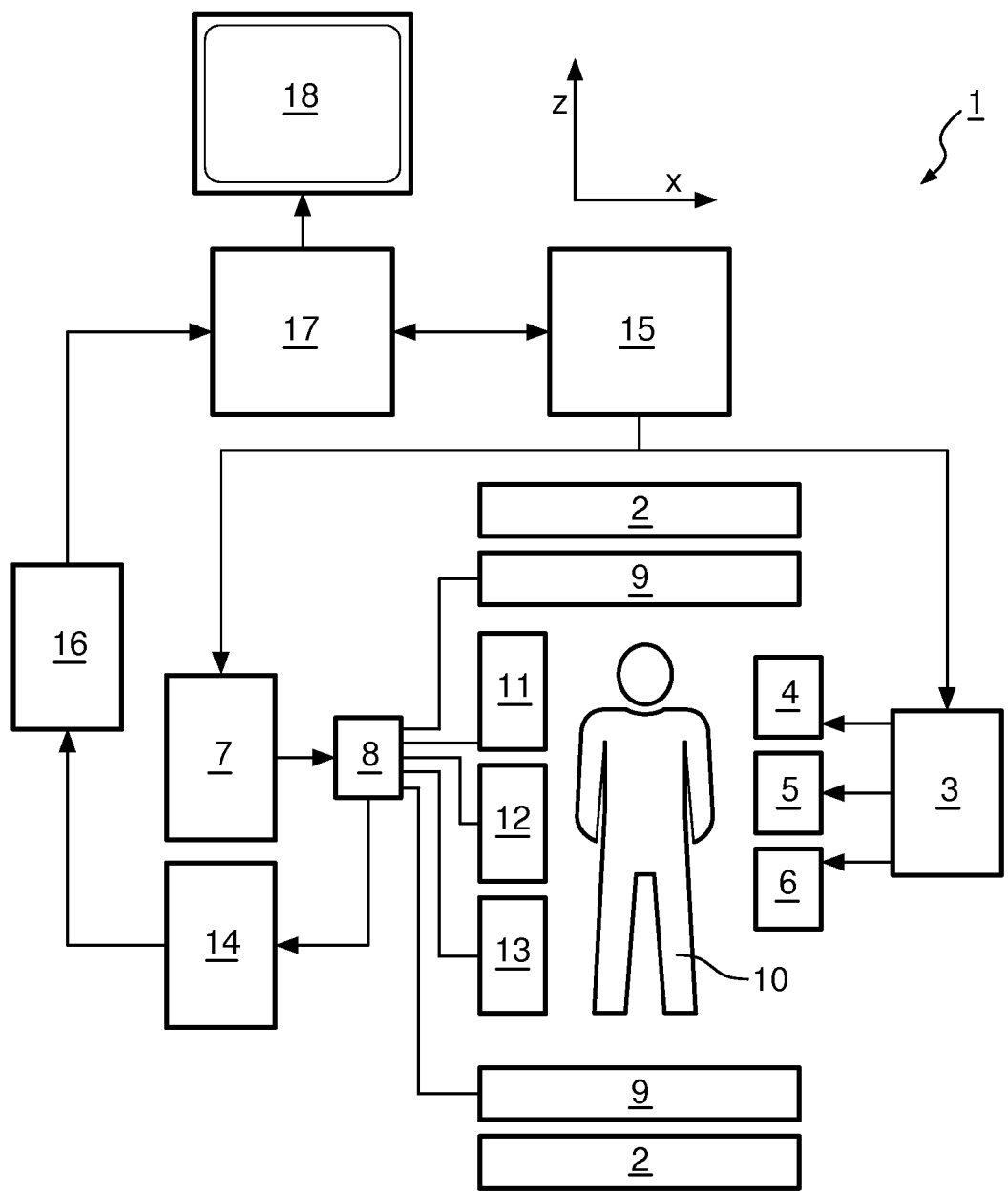
FIG. 1 shows an MR device for carrying out the method of the invention.

With reference to FIG. 1, an MR imaging system 1 is shown. The system comprises superconducting or resistive main magnet coils 2 such that a substantially uniform, temporarily constant main magnetic field $B_0$ is created along a z-axis through an examination volume.

A magnetic resonance generation manipulation system applies a series of RF pulses and switched magnetic field gradients to invert or excite nuclear magnetic spins, induce magnetic resonance, refocus magnetic resonance, manipulate magnetic resonance, spatially or otherwise encode the magnetic resonance, saturate spins and the like to perform MR imaging.

More specifically, a gradient pulse amplifier 3 applies current pulses to selected ones of whole body gradient coils 4, 5 and 6 along x, y and z-axes of the examination volume. An RF transmitter 7 transmits RF pulses or pulse packets, via a send/receive switch 8 to an RF antenna 9 to transmit RF pulses into the examination volume. A typical MR imaging sequence is composed of a packet of RF pulse sequences of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume, wherein the region of interest is defined within the examination volume, wherein the region of interest typically comprises at least a part of the body 10 or generally the object to be imaged. The MR signals may also be picked up by the RF antenna 9.

For generation of MR images of limited regions of the body or in general object 10, for example by means of parallel imaging, a set of local array RF coils 11, 12 and 13 are placed contiguous to the region selected for imaging. The array coils 11, 12 and 13 can be used to receive MR signals induced by RF transmissions effected via the RF antenna. However, it is also possible to use the array coils 11, 12 and 13 to transmit RF signals to the examination volume.

The resultant MR signals are picked up by the RF antenna 9 and/or by the array of RF coils 11, 12 and 13 and are demodulated by a receiver 14 preferably including a preamplifier (not shown). The receiver 14 is connected to the RF coils 9, 11, 12 and 13 via a send/receive switch 8.

A host computer 15 controls the gradient pulse amplifier 3 and the transmitter 7 to generate any of a plurality of imaging sequences, such as echo planar imaging (EPI), echo volume imaging, gradient and spin echo imaging, fast spin echo imaging and the like. For the selected sequence, the receiver 14 receives a single or a plurality of MR data lines in a rapid succession following each RF excitation pulse. A data acquisition system 16 performs analogue to digital conversion of the received signals and converts each MR data line to a digital format suitable for further processing.

In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, like for example Dixon reconstruction. The MR image may represent a planar slice through the patient, an array of parallel planar slices, a three-dimensional volume or the like. The image is then stored in an image memory where it may be accessed for converting slices or other portions of the image representation into appropriate formats for visualization, for example via a video monitor 18 which provides a man readable display of the resultant MR image.

In the following, an exemplary image reconstruction process employing the above described method shall be described in greater detail. The following procedure is proposed to consider a multi-peak spectral model of fat in the separation of a generic two-point method that does not impose any substantial constraints on the choice of the echo times.

The method starts with the acquisition of first and second echo data at different echo times $TE_n$, with n=1, 2, and a processing of said first and second echo data for reconstruction of a first and second image dataset $S_n$ by the reconstruction processor 17. Then, the composite complex signal S in image space for echo time $TE_n$, with n=1, 2, is modeled by:

$$S_n = (W + c'_n F) e^{i\phi_n}, \quad (9)$$

where W and F denote the either real or complex water and fat signal in image space, $\phi_n$ denotes the phase errors, and $e^{i\phi_n}$ denotes the corresponding phasors. As mentioned above, the phase errors include the phase due to the main field inhomogeneities and a static phase that may arise from RF penetration and signal delay in the receiver chain excluding a chemical shift induced phase due to the presence of fat.

The spectral signal model of fat is provided via the complex weighting coefficients (i.e. complex factors) c• given by:

$$c'_n = \sum_m w_m e^{i\theta_{n,m}}, \quad (10)$$

where w denotes weights that add up to one and $\theta_{n,m}$ equals $2\bullet\bullet f_m TE_n$, with $\bullet f_m$ being the offset in resonance frequency of the m-th peak of the fat spectrum with respect to water. Optionally, the influence of transverse relaxation may be included by adding a factor that describes the exponential decay with $TE_n$. The weights, the chemical shifts, and optionally the relaxation rates are assumed to be known a priori, either theoretically or experimentally, for example by a separate calibration process on the acquired MR images themselves.

In a subsequent step, two signal components are calculated from $S_1$ and $S_2$ pixel by pixel or voxel by voxel (3D pixel). This is performed by considering the two magnitudes of the acquired and the modelled image datasets obtained from Eq. (1):

$$|S_1|^2 = W^2 + 2c'_{1R} WF + (c'^2_{1R} + c'^2_{1I}) F^2, \quad (11)$$

$$|S_2|^2 = W^2 + 2c'_{2R} WF + (c'^2_{2R} + c'^2_{2I}) F^2, \quad (12)$$

Here, $c\bullet_{nR}$ and $c\bullet_{nI}$ denote the real and imaginary components of $c\bullet_n$. By employing the biquadratic equation $$a_1 F^4 + a_2 F^2 + a_3 = 0, \quad (13)$$

the two solutions $F_{1/2}$ $$F_{\frac{1}{2}} = \sqrt{-\frac{a_2}{2a_1} \pm \sqrt{\frac{a_2^2}{4a_1^2} - \frac{a_3}{a_1}}}, \quad (14)$$

may be derived. The constants a are given by:

$$a_1 = (c'^2_{1R} - c'^2_{1I} - 2c'_{1R} c'_{2r} + c'^2_{2R} + c'^2_{2I})^2 + 4(c'_{1R} - c'_{2R})^2 c'^2_{1I}, \quad (15)$$

$$a_2 = 2(c'^2_{1R} - c'^2_{1I} - 2c'_1 c'_{2R} + c'^2_{2R} + c'^2_{2I})(|S_1|^2 - |S_2|^2) - 4(c'_{1R} - c'_{2R})^2 |S_1|^2, \quad (16)$$

$$a_2 = (|S_1|^2 - |S_2|^2)^2. \quad (17)$$

The corresponding two solutions for $W_{1/2}$ are:

$$W_{1/2} = -c'_{1R} F \pm \sqrt{|S_1|^2 - c'^2_{1I} F^2}. \quad (18)$$

Consequently, a first and second species specific image dataset W and F can be obtained from said magnitudes calculated in Eqs. (11) and (12).

From the model of the first and second modelled image dataset Eq. (1) and the two pairs of values for W and F (Eqs. 14 and 18), two values for the phasor $\Delta P_{1/2} = e^{i(\Phi_2 - \Phi_1)}$ are obtained:

$$\Delta P_{\frac{1}{2}} = \frac{S^*_1 S_2}{\left(W_{\frac{1}{2}} + c'^*_1 F_{\frac{1}{2}}\right)\left(W_{\frac{1}{2}} + c'_2 F_{\frac{1}{2}}\right)}. \quad (19)$$

This results in two possible phasor candidates, one being true and one being false. The true phasor is extracted from the two phasor candidates through a procedure such as the regional iterative phasor extraction (RIPE) procedure. Additionally, the estimate of the true phasor may be adapted in view of the results obtained in a spatial neighbourhood of the pixel.

Given this estimate of the phasor, W and F are recalculated. This may, for instance, be done by solving a non-linear system of four equations for the real variables W and F, of which two are those for $|S_1|^2$ and $|S_2|^2$ in Eqs. (11) and (12) and two are the real and imaginary components of $$S^*_1 S_2 \Delta P^* = (W + c'^*_1 F)(W + c'_2 F). \quad (20)$$

Alternatively, a linear system of two equations may be solved for the complex variables W• and F•.

$$S_1 = W' + c'_1 F', \quad (21)$$

$$S_2 \Delta P^* = W' + c'_2 20 F'. \quad (22)$$

Since $W' = W e^{i\bullet}1$ and $F' = F e^{i\bullet}1$, the magnitude of W' and F' is equal to that of W and F.

Consequently, by carrying out the above described steps by the reconstruction processor 17, a good water-fat separation is achieved with a fast data acquisition method. Water and fat can be separated from just two complex valued images, none of which needs to be in phase.

Figure 2:
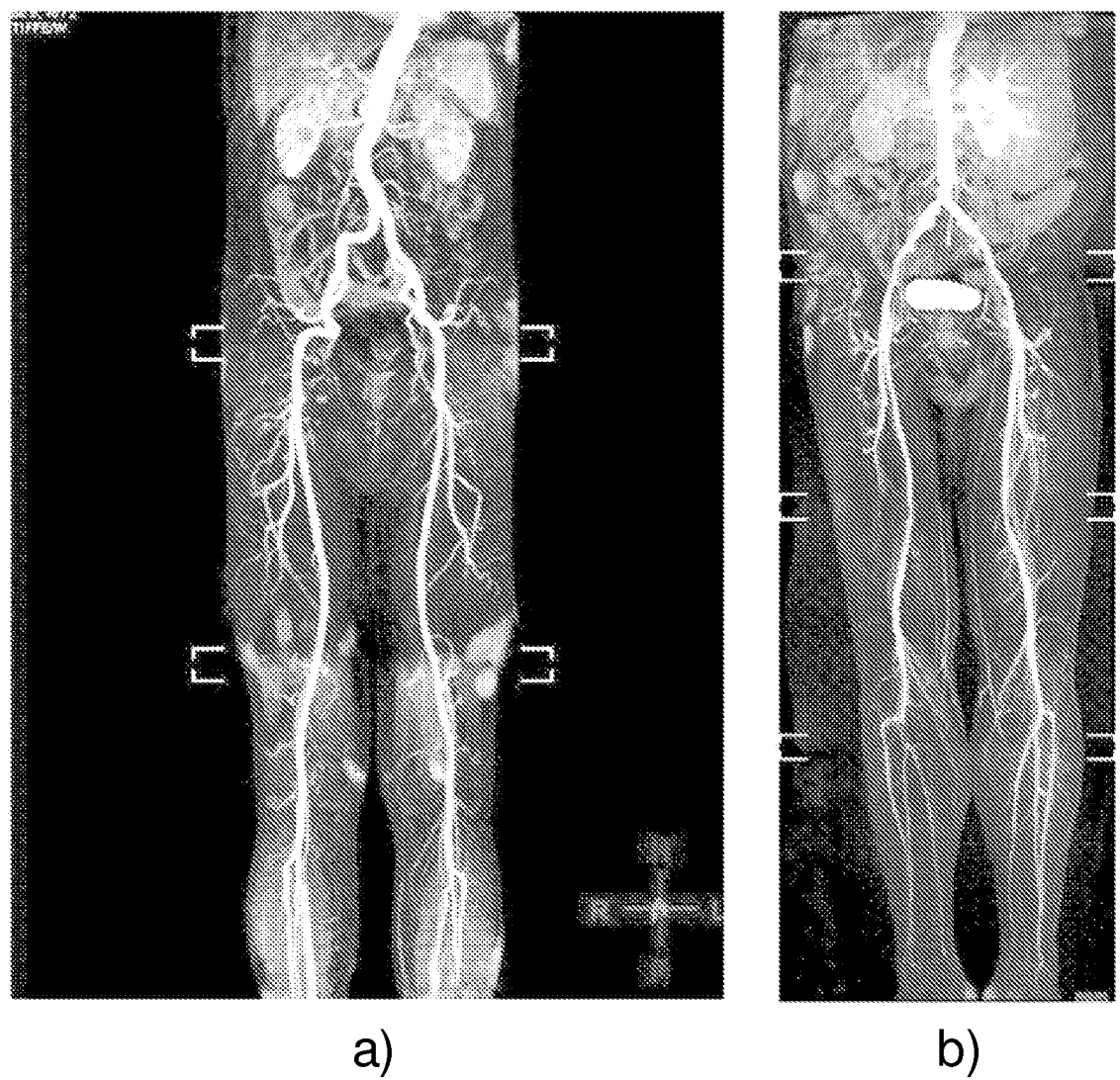
FIG. 2 shows CE-MRA images acquired using the method described above

FIG. 2 shows CE-MRA images acquired using the method described above. FIG. 2a was acquired using a 1.5 T MRI system and shows the peripheral vasculature acquired with a dual-gradient-echo data acquisition technique with flexible echo times and subsequent two-point Dixon water-fat separation ("mDixon approach"). FIG. 2b was acquired using a 3 T MRI system and shows also the peripheral vasculature. Data acquisition and image reconstruction is the same as in FIG. 1.

Thus, FIG. 2 illustrates that the above described method provides excellent MRA images at high resolution. In order to stress the advantages of this method more precisely, in the following a direct comparison to a regular Dixon approach is given: In case of the 1.5 T MRA system, the echo times for the two echoes required for CE-MRA using a regular Dixon approach would be TE1=2.3 ms and TE2=4.6 ms. This is because of the requirement of using exactly in- and out-of-phase echo times. As a result, at clinically relevant resolution the respective TR would be around 6.1 ms.

In comparison thereto, CE-MRA using the above described mDixon approach permits to use flexible echo times for the two echoes with TE1=1.8 ms and TE2=3.0 ms. At clinically relevant resolution the respective TR will be around 4.3 ms, which corresponds to a 40% shortened scan time compared to the regular Dixon approach.

Similarly, in case of the 3 T MRI system, the echo times for the two echoes required for CE-MRA using a regular Dixon approach would be TE1=2.3 ms and TE2=3.5 ms. This is because of the requirement of using exactly in- and out-of-phase echo times. As a result, at clinically relevant resolution the respective TR will be around 5.2 ms.

In comparison thereto, CE-MRA using the above described mDixon approach permits to use flexible echo times for the two echoes with TE1=1.6 ms and TE2=2.8 ms. At clinically relevant resolution the respective TR will be around 4.5 ms, which corresponds to a 14% shortened scan time compared to the regular Dixon approach.

Since the total scan time in a typical CA-MRA scan is about 15 seconds, a 40% increase in scan time is intolerable in case it is desired to maintain a high image resolution. This problem is solved with the above described method of using flexible echo times.

Further, it has to be noted that because of the prohibitively long TE2 values of the conventional Dixon approach, signal dephasing might occur. This is also avoided by employing the above described method of using flexible (and thus shorter) echo times.

Figure 3:
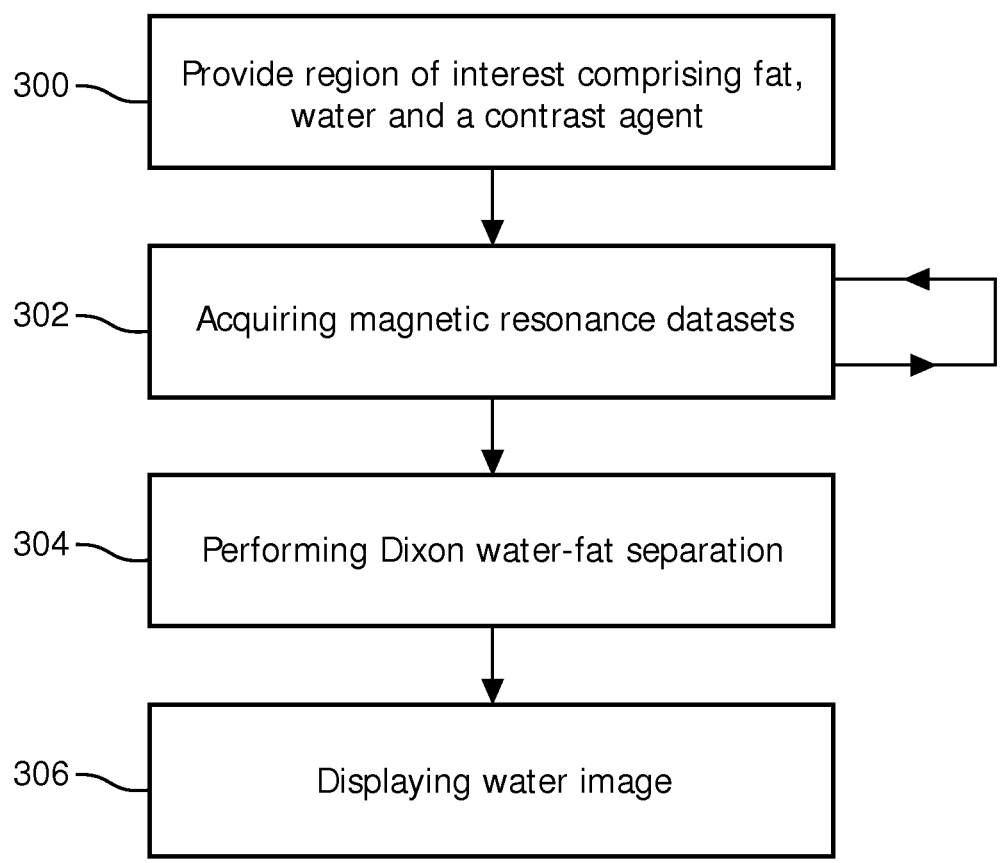
FIG. 3 is a flowchart illustrating the method of the invention.

FIG. 3 is a flowchart illustrating the method according to the invention. In step 300 an object is provided within the examination zone of the MR scanner. Within the examination zone a region of interest is defined, wherein the region of interest covers at least partially a region of the object which comprises water due to the presence of blood, fat and a contrast agent.

In step 302, magnetic resonance datasets of a region of interest are acquired using a single- or multi-echo data acquisition technique, wherein the echo times of the one or multiple echoes are flexible. Performing of step 302 takes a time duration equivalent to TR, such that step 302 is continuously repeated in order to accumulate datasets until a maximum total time is reached. This time is defined by the tolerable time in which the presence of the contrast agent is ensured at a predefined level within the region of interest. However, the time may be further limited by movements occurring in the region of interest like breathing induced movements or heart beat induced movements.

After completion of step 302, the method continues with step 304 performing processing of the datasets acquired in step 302 using a generalized Dixon water-fat separation technique to eliminate the signal originating from the fat from the background for reconstruction of an image data set. Finally, the method ends in step 304 with displaying the reconstructed water image data set.

The invention claimed is:

1. A method of performing contrast enhanced first pass magnetic resonance angiography, the method comprising:
   acquiring magnetic resonance datasets of a region of interest, during a first pass of contrast agent through the region of interest after intravenous injection of the contrast agent, using a multi-echo data acquisition technique using multiple echoes, wherein echo times of the multiple echoes are flexible in that the echoes are not fixed to times at which a water signal originating from water and a fat signal originating from fat are in-phase or opposed-phase, and wherein the region of interest comprises fat, water and the contrast agent during the multi-echo data acquisition; and
   processing the datasets using a modified Dixon water-fat separation technique to eliminate the fat signal originating from the fat from background of the region of interest to reconstruct a magnetic resonance angiographic image data set.

2. The method of claim 1, wherein the multi-echo data acquisition technique is a dual-gradient-echo data acquisition technique and the modified Dixon water-fat separation technique is a two-point Dixon technique with the flexible echo times.

3. The method of claim 1, wherein the acquisition of the magnetic resonance datasets comprises acquiring first and second echo data at the two different echo times resulting in first and second signal datasets, wherein the first and second echo data are acquired in one time of repetition.

4. The method of claim 3, wherein the processing of the datasets comprises:
   calculating first and second components, or ratios or fractions of the first and second components, from the first and second signal datasets,
   deriving two differential phase error candidates from the first and second components,
   selecting, for each pixel, one of the derived differential phase error candidates, based on an assumption of smoothness of disturbing field inhomogeneity; and
   reconstructing a water image using the selected differential phase error candidate.

5. The method of claim 3, wherein the first and second signal datasets are first and second acquired complex signal datasets, and wherein the processing of the datasets comprises:
   modelling the first and second acquired complex signal datasets by employing a spectral signal model of fat, the modelling of fat resulting in first and second modelled complex signal datasets, the first and second modelled datasets comprising first and second phase errors and the separate signal datasets for water and fat; and
   determining from the first and second acquired complex signal datasets and the first and second modelled complex signal datasets the separate signal dataset for water.

6. A computer program product comprising computer executable instructions to perform the method steps as claimed in claim 1.

7. A magnetic resonance imaging apparatus for performing contrast enhanced first pass magnetic resonance angiography, the apparatus comprising:
   a data acquisition system for acquiring magnetic resonance datasets of a region of interest, during a first pass of contrast agent through the region of interest after intravenous injection of the contrast agent, using a multi-echo data acquisition technique using multiple echoes, wherein echo times of the multiple echoes are not fixed to times at which a water signal originating from water and a fat signal originating from fat are in-phase or opposed-phase, and wherein the region of interest comprises fat, water and the contrast agent during the multi-echo data acquisition; and a reconstruction processor for processing the datasets using a modified Dixon water-fat separation technique to eliminate the fat signals signal originating from the fat from-the background for reconstruction of a magnetic resonance angiographic image data set.

8. The apparatus of claim 7, wherein the multi-echo data acquisition technique is a dual-gradient-echo data acquisition technique and the modified Dixon water-fat separation technique is a two-point Dixon technique with the flexible echo times.

9. The apparatus of claim 7, wherein the data acquisition system acquiring the magnetic resonance datasets comprises acquiring first and second echo data at the two different echo times resulting in first and second signal datasets, wherein the first and second echo data are acquired in one time of repetition.

10. The apparatus of claim 9, wherein the reconstruction processor processing the datasets comprises:

calculating first and second components, or ratios or fractions of the first and second components, from the first and second signal datasets;

deriving two differential phase error candidates from the first and second components, selecting, for each pixel, one of the derived differential phase error candidates, based on an assumption of smoothness of disturbing field inhomogeneity; and reconstructing a water image using the selected differential phase error candidate.

11. The apparatus of claim 9, wherein the first and second signal datasets are first and second acquired complex signal datasets, and wherein the processing of the datasets comprises:

modelling the first and second acquired complex signal datasets by employing a spectral signal model of fat, the modelling of fat resulting in first and second modelled complex signal datasets, the first and second modelled datasets comprising first and second phase errors and the separate signal datasets for water and fat; and determining from the first and second acquired complex signal datasets and the first and second modelled complex signal datasets the separate signal dataset for water.

* * * * *